United States Patent
Koch (10) Patent No.: US 11,813,207 B2
(45) Date of Patent: Nov. 14, 2023

(54) MEDICAL SUPPORT ARM WITH LOCKABLE PIVOT JOINT

(71) Applicant: MAQUET GMBH, Rastatt (DE)

(72) Inventor: Guido Koch, Karlsruhe (DE)

(73) Assignee: MAQUET GMBH, Rastatt (DE)

( * ) Notice: Subject to any disclaimer, the term of this patent is extended or adjusted under 35 U.S.C. 154(b) by 949 days.

(21) Appl. No.: 16/683,984

(22) Filed: Nov. 14, 2019

(65) Prior Publication Data

US 2020/0085664 A1 Mar. 19, 2020

Related U.S. Application Data

(63) Continuation of application No. PCT/EP2018/061345, filed on May 3, 2018.

(30) Foreign Application Priority Data

May 17, 2017 (DE) .................... 10 2017 110 718.5

(51) Int. Cl.
  *A61G 13/12* (2006.01)
  *A61B 90/50* (2016.01)

(52) U.S. Cl.
  CPC ............ *A61G 13/125* (2013.01); *A61B 90/50* (2016.02); *A61B 2560/04* (2013.01); *A61G 2203/78* (2013.01)

(58) Field of Classification Search
  CPC .............. A61G 13/125; A61G 2203/78; A61G 13/0081; A61G 13/101; A61B 90/50; A61B 2560/04; A61B 2090/508; A61B 2090/571; A61B 90/57
  See application file for complete search history.

(56) References Cited

U.S. PATENT DOCUMENTS

| | | | | |
|---|---|---|---|---|
| 5,802,641 | A | * 9/1998 | Van Steenburg | A61G 13/12 5/624 |
| RE41,412 | E | * 7/2010 | Van Steenburg | A61G 13/0009 5/624 |
| 2003/0028967 | A1 | * 2/2003 | Schuerch | A61G 13/12 5/621 |
| 2004/0133979 | A1 | 7/2004 | Newkirk et al. | |
| 2007/0265635 | A1 | * 11/2007 | Torrie | A61G 13/0081 606/105 |

(Continued)

OTHER PUBLICATIONS

International Search Report dated Jul. 2, 2018 during the prosecution of corresponding PCT application No. PCT/EP2018/061345, 2 pages.

*Primary Examiner* — Myles A Throop (57) ABSTRACT

A medical support arm may include a holding end, a coupling end, a coupling-end pivot joint for swiveling the support arm about a pivot axis (A1) and tilting the support arm about a tilt axis (A2), and a clamping mechanism with which the pivot joint can be locked or released as desired. The pivot joint allows the support arm to rotate exclusively about the tilt axis (A2) and the pivot axis (A1). A tilting device may have a tilting element and a cylindrical sliding surface on which the tilting element is seated. A pivot mechanism can have a guide ring and at least one ring guide surface that receives the guide ring. A tilting element, as part of the clamping mechanism, may be provided as a gripper clamp that secures both the tilting device and the pivot mechanism against rotation by clamping the central body.

19 Claims, 4 Drawing Sheets

(56) References Cited

U.S. PATENT DOCUMENTS

| | | |
|---|---|---|
| 2013/0191994 A1 | 8/2013 | Bellows et al. |
| 2015/0342813 A1* | 12/2015 | Catacchio .......... A61G 13/1205 5/630 |
| 2017/0281447 A1* | 10/2017 | Lane, II ............. A61G 13/1295 |
| 2019/0254905 A1* | 8/2019 | Lane, II ............. A61G 13/1235 |

* cited by examiner

MEDICAL SUPPORT ARM WITH LOCKABLE PIVOT JOINT

RELATED FILINGS

Priority and benefit are claimed to German application DE102017110718.5 (filed May 17, 2017) and to PCT/EP2018/061345 (filed May 3, 2018), both of which are incorporated herein.

BACKGROUND

The present disclosure relates to a medical support arm.

One exemplary support arm is offered by the company Mizuho OSI as part of an operating table. The operating table is sold under the trademark ProFx. A presentation of the ProFx operating table can be found on the internet.

The Mizuho OSI support arm is connected to the operating table by means of a ball joint with ball and ball socket. The ball joint enables the support arm to be rotated in different directions. The surgeon can thus bring the position of a patient's leg, which is attached to the support arm, into the optimal position for the procedure. When the patient's leg is properly aligned, the support arm can be locked in place by means of a clamping mechanism. For this purpose, the ball socket is mechanically clamped on the ball. More precisely, a rotary lever located at the end of the support arm is folded, whereby it acts on the ball socket via a torsion shaft that is arranged inside the bar.

This type of support arm has the following disadvantages:
The user has to apply a strong closing force with the lever. In addition, only one fixed adjustment path is available for the lever, and the user has to trust that the bias generated over the adjustment path between ball socket and ball is sufficient and the support arm is thus fixed securely in place;
ball and ball socket run dry against one another with a high coefficient of friction; accordingly, at least one of the friction partners wears during use as a result of the rotations of the support arm;
because of the wearing of the friction partners, the clamping mechanism must be regularly adjusted so that the rotary lever always moves in the same range;
the exposed ball surface gets dirty, and the dirt can be conveyed into the joint, which can eventually lead to failure of the ball joint; and
since the user has to bear the load of the support arm with one hand while performing the closing operation with considerable effort with the other hand when the support arm is in the unlocked state, there is a risk of the support arm and thus the patient's leg falling accidentally before the support arm is securely locked.

Another support arm is described in WO 2007/080454 A2. This support arm is marketed by Smith & Nephew as part of a hip positioning system.

This support arm can also be rotated via a lockable ball joint; see FIGS. 5 and 6 of WO 2007/080454 A2. The ball joint is locked and released by means of a rotary knob located at the end of the support arm. The ball joint apparently locks automatically when the user accidentally releases the support arm.

This type of support arm has the following disadvantages:
As with the Mizuho OZI support arm, regular adjustment of the clamping mechanism is required because of the wear on the ball surface;
likewise, there is the problem with the contamination of the ball surface; and
when used on the operating table, the ball joint and support arm interfere with the free positioning of a C-arm and X-ray imaging of the patient, because they are in the way and not permeable to X-rays.

Accordingly, it is desirable to improve these known support arms such that they are safer, lower-maintenance, and easier to lock and unlock.

It is therefore an object of the present disclosure to provide a medical support arm with lockable pivot joint in which the pivot joint is reliable, low-maintenance, and easy to lock and unlock during everyday use.

SUMMARY OF THE DISCLOSURE

By virtue of the design of the pivot joint as a central body encompassed by a tilting and clamping mechanism with separate tilting and pivot mechanism, it is possible to apply a strong clamping force in a targeted manner to the pivot joint.

In past solutions with a ball joint, the clamping is based in all directions exclusively on the frictional resistance generated between the ball and the ball socket and is directly dependent on the diameter thereof. This frictional resistance becomes more and more unreliable over time due to wear on the ball and contamination of the ball surface.

In the present disclosure, by contrast, the clamping is preferably based on two separate components: the frictional resistance between ring guide surface of the central body and guide ring on the one hand, and the frictional resistance between the cylindrical sliding surface of the central body and tilting element/gripper clamp on the other hand. In the present disclosure, the guide ring can be kept small because low torques can be expected in the swiveling movement. The substantially higher torques in the tilting direction are preferably absorbed by the gripper clamp, which acts as a tilting element and has a commensurately adapted, typically larger diameter. When in the clamped state, the gripper clamp need only withstand torques in the tilting direction and not absorb torques of any kind that can act on the support arm, as is required in the case with the ball socket that is known from the aforementioned prior art.

What is more, the friction surfaces of the pivot joint are subjected to less wear due to the claimed construction of the present disclosure. And because they are sealed off the environment, they also cannot get dirty. Accordingly, the risk of failure of the pivot joint and the associated maintenance costs are substantially reduced.

In particular, the friction surfaces can be lubricated with oil, so that no appreciable wear occurs. Moreover, the friction surfaces can be completely enclosed, thereby preventing dirt from getting in or lubricant from getting out.

Any and all features disclosed herein can be combined with one another in any desired manner insofar as is technically possible.

The disclosure also relates to an operating table having a medical support arm, and to methods of use and operation of support arms and operating tables. The medical support arm most typically includes an extension bar, but can also take other forms.

The disclosure includes, for example, medical support arms and operating tables having some or all of the following features:
a holding end for gripping and operating the support arm;
a coupling end for connecting the support arm to a patient support, such as an operating table;

a coupling-end pivot joint for swiveling the support arm about a pivot axis (A1) and tilting the support arm about a tilt axis (A2) that intersects with the pivot axis;

a clamping mechanism with which the pivot joint can be selectably: a) locked so that a rotation of the support arm both about the pivot axis and the tilt axis is prevented; and b) released so that the support arm can rotate freely about both axes (A1, A2);

a release lever located at the holding end for releasing the clamping mechanism;

a support bar for supporting a medical device that extends between the holding end and the coupling end; and/or a force transmission device that is arranged in and/or on the support bar for transmitting a releasing force from the release lever to the clamping mechanism, wherein the pivot joint:
a) allows the support arm to rotate exclusively about the tilt axis (A2) and the pivot axis (A1);
b) comprises a tilting device for tilting the support arm about the tilt axis (A2), the tilting device comprising a tilting element and a cylindrical sliding surface on which the tilting element is seated, so that the cylindrical sliding surface and the tilting element can rotate relative to one another about the tilt axis (A2);
c) a pivot mechanism for swiveling the support arm about the pivot axis (A1), the pivot mechanism having a guide ring and at least one ring guide surface receiving the guide ring, so that the guide ring and the at least one ring guide surface can rotate relative to one another about the pivot axis (A1); and/or
d) comprises a central body that is located in the center of the pivot joint and on which the cylindrical sliding surface and the at least one ring guide surface are formed;

wherein the tilting element, as part of the clamping mechanism, also acts as a gripper clamp in such a way that it secures both the tilting device and the pivot mechanism against rotation by clamping the central body.

In some embodiments, the cylindrical sliding surface extends once completely around the tilt axis (A2). The central body may comprise two mutually mirror-inverted guide bodies, wherein a ring guide surface for the guide ring is formed in each guide body, and wherein a portion of the cylindrical sliding surface is formed on the outside of each guide body, so that the two parts together form the entire cylindrical sliding surface.

The central body may have a cavity in its interior for receiving the guide ring.

The medical support arm may include a connecting piece at the holding end, wherein the connecting piece supports the guide ring and has a coupling for connecting to the patient support.

A guide ring could be received between the prongs of a forked end of the connecting piece.

The clamping mechanism may include a spring assembly that biases the clamp into the locked position.

A clamp mechanism optionally further comprises an eccentric assembly via which the spring assembly acts on the gripper clamp.

A spring assembly can include at least one disc spring, wherein the eccentric assembly comprises at least one eccentric lever. Each eccentric lever may have an eccentric end in the form of an eccentric disc and an operating end, wherein the operating end is connected to a disc spring, and wherein the eccentric end is connected to an extremity of the gripper clamp through which the axis of rotation (Y-Y) of the eccentric lever passes.

In some embodiments the force transmission device comprises:
a master cylinder that is arranged at the holding end;
a slave cylinder that is arranged at the coupling end; and/or
a hydraulic line that extends through the interior of the support bar and connects the master cylinder to the slave cylinder.

Optionally the slave cylinder hydraulically releases the bias of the spring assembly upon actuation of the release lever.

In some embodiments the pivot axis (A1) and the tilt axis (A2) are each aligned perpendicular to a longitudinal axis (X-X) of the medical support arm and perpendicular to each other.

The medical support arm can include a hand grip at the holding end that is arranged so as to be adjacent to the release lever, so that, particularly when the clamp mechanism is released, the medical support arm can be held by a person with one hand on the release lever and the other hand on the hand grip.

In a useful embodiment:
the medical support arm is an extension bar;
the extension bar has a carriage thereon, the carriage being slideable axially along the extension bar; and/or
the carriage carries a device shaped for holding the foot of a patient.

BRIEF DESCRIPTION OF THE DRAWINGS

Exemplary embodiments of the present disclosure will now be described with reference to the accompanying drawings, in which like reference symbols designate same or analogous elements, respectively.

DETAILED DESCRIPTION

In the following description, exemplary embodiments of the present disclosure will be described with reference to the drawings. The drawings are not always necessarily to scale, but are intended to illustrate the respective features only schematically.

It should be noted that the features and components described herein can be combined with one another regardless of whether they have been described in connection with a single embodiment. The combination of features in the respective embodiments is merely illustrative of the basic construction and functionality of the claimed device.

Figure 1:
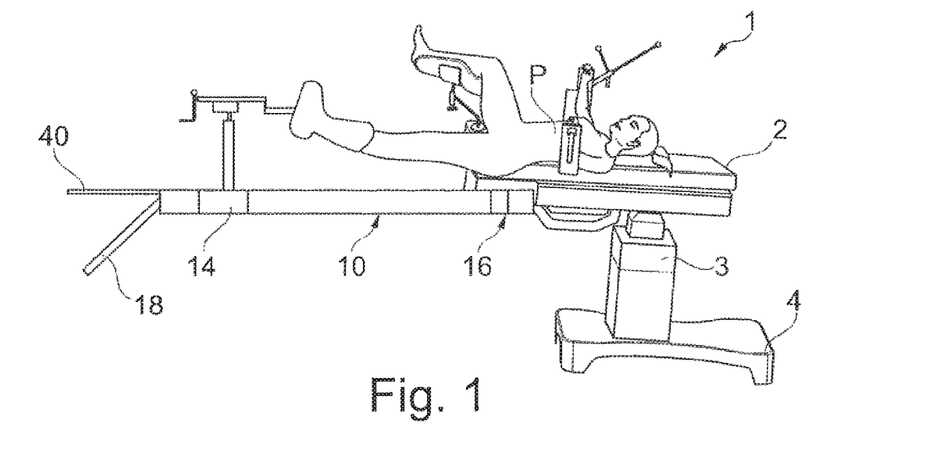
FIG. 1 shows a representation of an operating table according to the disclosure.

As shown in FIG. 1, an operating table 1 comprises a patient support surface 2, a post 3, and a base 4. To perform orthopedic operations, a medical support arm 10—in this case an extension bar—can be used by means of which the leg of a patient P can be fixed in a desired position, it being possible both to exert pulling forces on the leg and to rotate the leg about its longitudinal axis.

By means of a pivot joint 16, the extension bar 10 can be aligned and fixed in place relative to the operating table 1, or generally relative to a structure to which an end of the extension bar is attached.

It should be emphasized that, according to the disclosure, when the pivot joint 16 is in the state in which it is mounted on the operating table 1 (see FIG. 1), it may advantageously be located as far as possible toward the head of the patient P. In particular, the pivot joint 16 is can be located at least at hip level or even above the hip of the patient as seen in the direction of the head. As a result, the pivot joint is located outside of the area that is technically of interest for radiography when the patient's hip needs to be X-rayed using a C-arm. The extension bar 10 is preferably made of a material that is transparent to the radiation used in for imaging. In the solution that is known from WO 2007/080454 A2, the pivot joint is located below the patient's crotch, which makes imaging by means of a C-arm more difficult.

Figure 2:
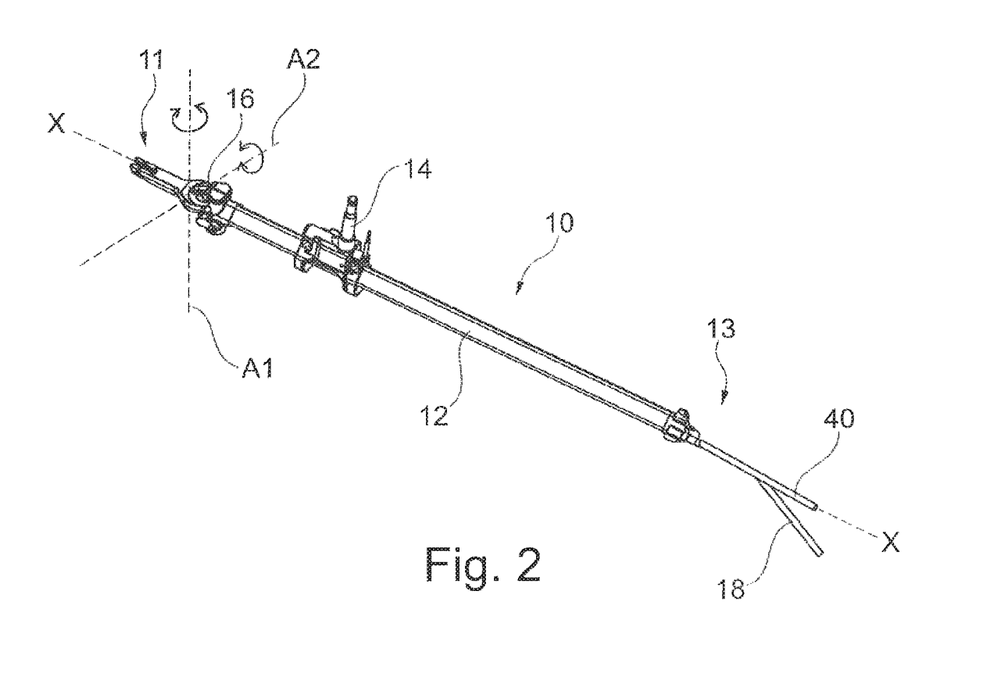
FIG. 2 shows a medical support arm with lockable pivot joint according to one embodiment of the present disclosure.

The support arm 10 shown in FIG. 2 comprises a support bar 12 on which a carriage 14 is mounted. The carriage 14 can be moved along the longitudinal axis X-X of the support bar 12. For example, holding fixtures can be attached to the carriage 14 in order to secure a patient's foot (see FIG. 1). The holding fixture will then also be movable along the support bar. Preferably, the support bar 12 is made of material that is permeable to X-ray radiation. Consequently, the support beam 12 need not be removed from the region to be X-rayed during X-raying of the patient P, since it does not appear in the subsequent X-ray image. For example, the support bar 12 can be made of carbon fiber composite.

A pivot joint 16 is mounted at a first coupling end 11 of the support arm 10 by means of which the support arm 10 can be rotated about two axes relative to the operating table 1. The pivot joint 16 is thus a cardan joint that defines a pivot axis A1 about which the support arm 10 can be swiveled in the horizontal as well as a tilt axis A2 about which the support arm 10 can be tilted in the vertical.

A release lever 18 can be mounted for example at a second holding end 13 of the support arm 10 by means of which the pivot joint 16 can be locked or released. In addition to the release lever 18, a hand grip 40 is provided. A user can thus stand at the foot end of the patient, grab the hand grip 40 with one hand and pull the release lever 18 up with the other hand and hold it there in order to release the pivot joint 16 so that he can position the patient's leg in a desired position in space. Once the desired position has been reached, the user can release the pivot joint 16 by releasing the release lever 18 again as described below.

The release lever 18 is rotated upward about the tilt axis A2 when it is raised.

Figure 3:
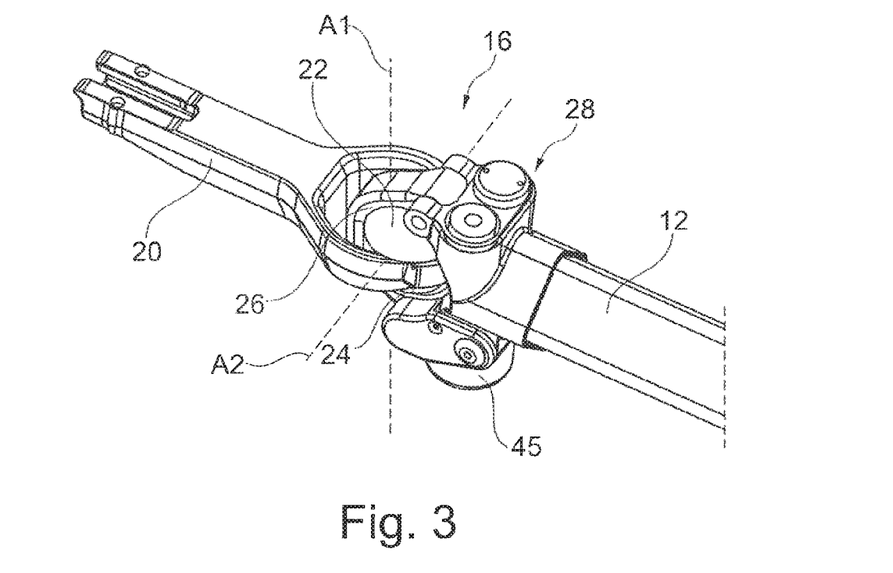
FIG. 3 shows a detailed view of the pivot joint in the support arm that is shown in FIG. 2.
Figure 5:
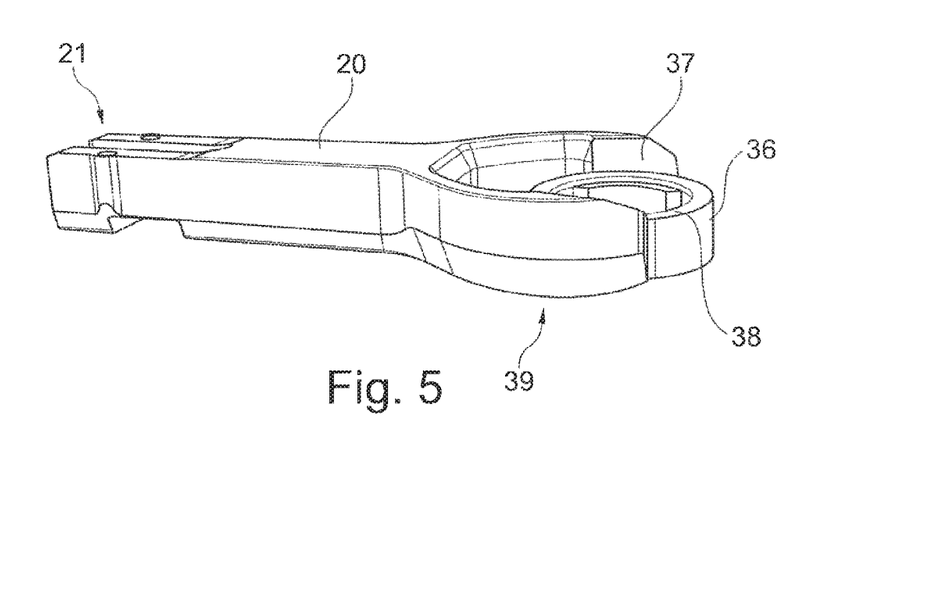
FIG. 5 shows a connecting piece of the support arm from FIG. 2.
Figure 6:
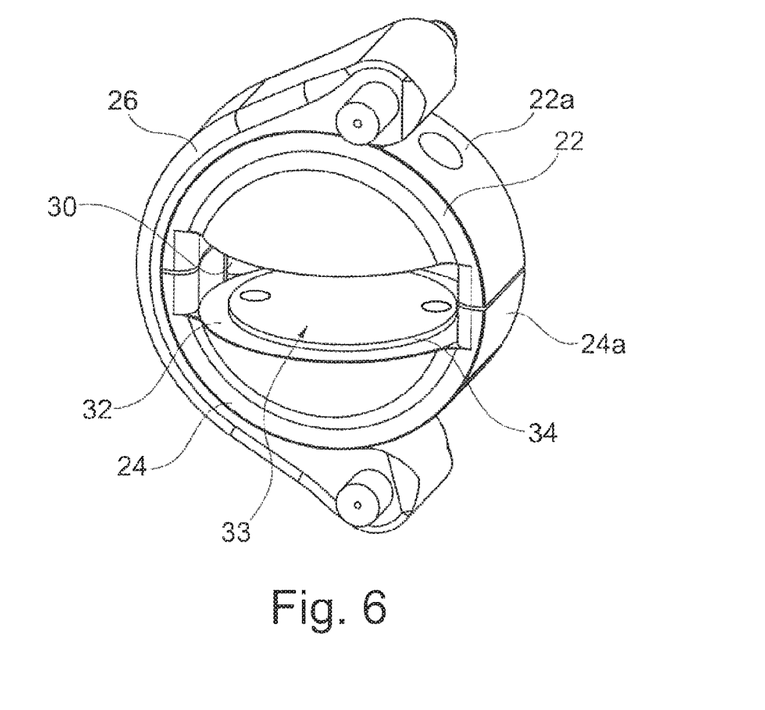
FIG. 6 shows the central body as well as the gripper clamp of the pivot joint from FIG. 3, which acts as a tilting element.

FIGS. 3, 5, and 6 show the pivot joint 16 as well as a connecting piece 20 that can be connected to the operating table 1 by means of a plug connection or the like, for example. The connecting piece 20 has a coupling 21 for this purpose.

The pivot joint 16 comprises a guide ring 36, a central body 22, and a gripper clamp 26. The central body consists of two mutually mirror-inverted guide bodies 22, 24. The guide bodies 22, 24 define between them a cavity 33 for receiving the guide ring 36.

The guide ring 36 is received between the two guide bodies 22, 24 so as to be rotatable about the pivot axis A1. It rests with his two flat surfaces against the corresponding ring guide surfaces 30, 32. The guide ring 36 is received between the prongs 37 of a forked end 39 of the connecting piece 20.

The gripper clamp 26, which is securely connected to the support bar 12, can be mounted on a cylindrical sliding surface 22a, 24a of the central body 22, 24 so as to be rotatable about the tilt axis A2. The gripper clamp 26 and the cylindrical sliding surface 22a, 24a together form a tilting device for tilting the support arm 10 about the tilt axis A2. The gripper clamp 26 thus constitutes a tilting element.

As part of a clamping mechanism 28, the gripper clamp 26 can be tightened around the guide bodies 22, 24 in such a way that both a rotation of the gripper clamp 26 relative to the guide bodies 22, 24 and a rotation of the guide ring 36 relative to the guide bodies 22, 24 is prevented.

The pressure that is exerted by the gripper clamp 26 on the two guide bodies 22, 24 is exerted in like manner by the guide bodies 22, 24 on the flat surfaces of the guide ring 36.

As can be seen particularly from FIG. 6, the two guide bodies 22, 24 are pressed by the gripper clamp 26 against each other and by means of respective contact surfaces in the form of ring guide surfaces 30, 32 between the guide bodies 22, 24 onto the guide ring 36 (not shown in FIG. 6), so that the pivot joint 16 is fixed in both axes of rotation A1, A2.

The ring guide surfaces 30, 32 form together with the guide ring 36 a pivot mechanism for swiveling the support arm 10 about the pivot axis A1.

Furthermore, it can be seen in FIG. 6 that the ring guide surfaces 30, 32 of the guide bodies 22, 24 can be configured with one or more circular arc-shaped guide projections 34 in order to guide the rotational movement of the guide ring 36 about the pivot axis A1 between the guide bodies 22, 24. FIG. 6 shows a single, circular guide projection 34, but it is also conceivable for a plurality of guide projections 34 to be provided, each of which corresponds to a circular arc portion.

As shown in FIG. 5, the connecting piece 20 comprises the guide ring 36, whose respective end surfaces 38 serve as contact surfaces between the connector 20 and the guide bodies 22, 24 and engage in the inner edge of the guide projection(s) 34 of the guide bodies 22, 24.

Alternatively, guide projections or other guide means can also be provided on the contact surfaces 38 of the guide ring 36. In another embodiment, the contact surfaces 38 can also be conical or spherical. They should have a tensioning effect when an axial force is applied to the pivot axis.

Figure 4:
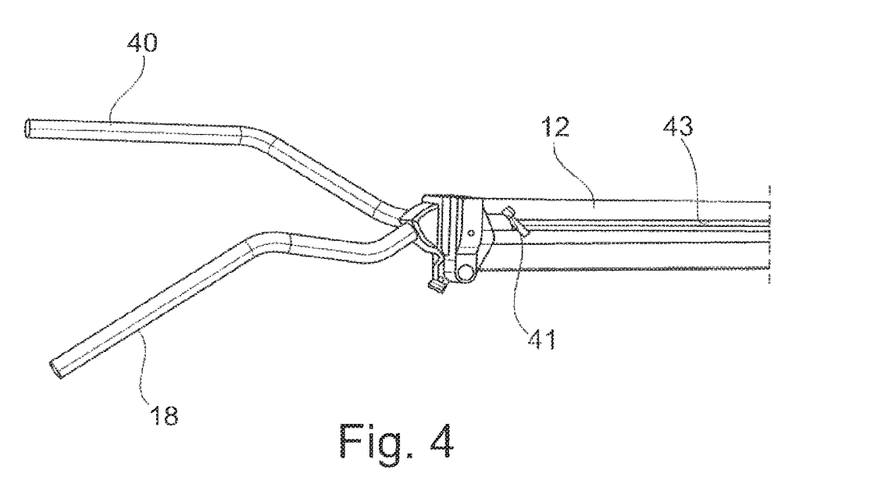
FIG. 4 shows a release lever that can be used in the support arm that is shown in FIG. 2.

The release lever 18 is shown in FIG. 4. In the present embodiment, a pair of levers or handles is provided, it being possible for a user to pull the movable release lever 18 to a rigid hand grip 40. This enables the user to support and move the weight of the bar 12 and of a patient's leg attached thereto, for example, by means of the rigid hand grip 40 while simultaneously opening the clamping mechanism 28 with the release lever 18. When the movable release lever 18 is raised to the stop, the load of the patient's leg is borne by both of the user's hands, which minimizes the risk of unwanted lowering. This contributes to safe use. In such an operation, hydraulic fluid is conducted from a master cylinder 41, which is mounted in the immediate vicinity of the release lever 18, via a hydraulic line 43 that extends in the bar 12 to a slave cylinder 45 (see FIG. 7), so that the clamping mechanism 28 is moved from its locked home position into a release position. The two hydraulic cylinders 41, 45 form a force transmission device together with the hydraulic line 43.

Figure 7:
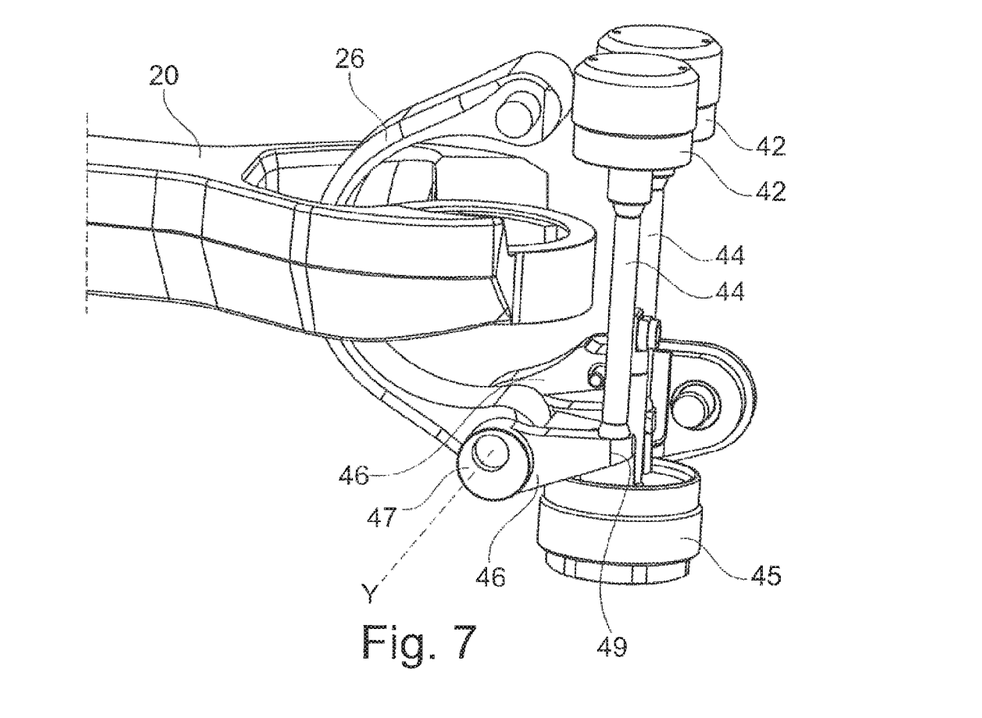
FIGS. 7 and 8 illustrate the clamping mechanism of the support arm from FIG. 2.

In the locked home position shown in FIG. 7, disc spring assemblies 42 press associated eccentric levers 46 by means of push rods 44 into a position in which they pull an extremity of the gripper clamp 26 in a tangential direction, thereby pressing the gripper clamp 26 onto the cylindrical sliding surface of the guide bodies 22, 24 such that the movement of the pivot joint 16 is locked about both axes of rotation A1, A2.

The clamping mechanism 28 thus comprises the clamp 26, the disc spring assemblies 42, the push rods 44, and the eccentric levers 46. The two eccentric levers 46 are arranged on either side of the gripper clamp 26. In the present case, they are connected by a web, because they have to perform the same movement together. The two eccentric levers 46 form a unitary component with the connecting web.

Each eccentric lever 46 has an eccentric end 47 in the form of an eccentric disc and an operating end 49. The axis of rotation Y-Y of the eccentric levers 46 extends through an extremity of the gripper clamp 26. The eccentric axis of rotation Y-Y is parallel to the tilt axis A2.

The gripper clamp 26 is thus actuated by the swiveling eccentric levers 46 in order to effect a force transmission in the direction of the gripper clamp 26. At the long lever of the eccentric 46, the disc spring assembly 42 exerts compressive force via the associated push rod 44 and thus generates the required closing force in the idle state.

Figure 8:
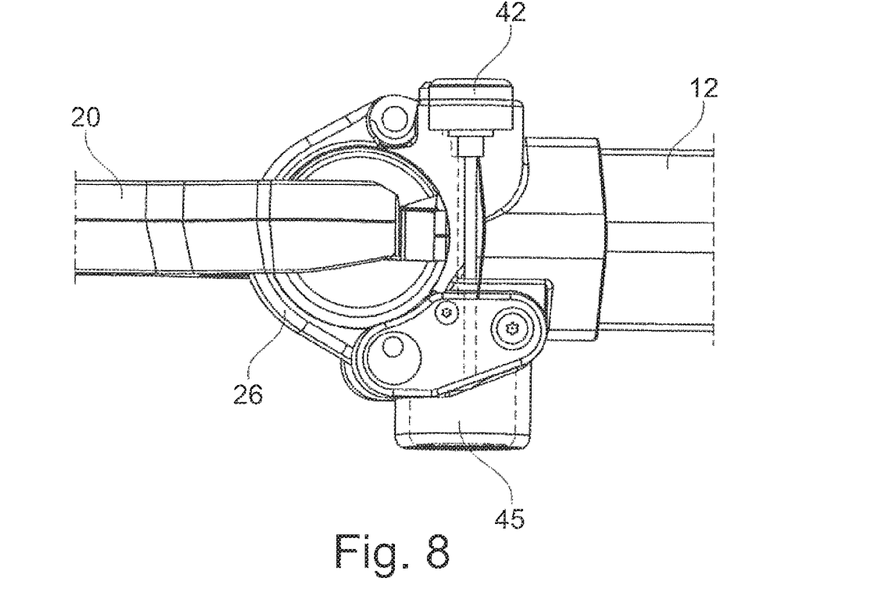

Upon actuation of the release lever 18, the clamping mechanism 28 is moved from the locked home position shown in FIGS. 7 and 8 into a release position in which a movement of the connecting piece 20 about the pivot axis A1 and a movement of the gripper clamp 26 about the tilt axis A2 relative to the guide bodies 22, 24 (see FIG. 3) is made possible by the fact that the eccentric levers 46 are moved against the spring force of the disc spring assemblies 42, so that the pressure of the gripper clamp 26 is dissipated to the lateral surfaces of the guide bodies 22, 24, with the effect that the gripper clamp 26 and the connecting piece 20 can be moved relative to the guide bodies 22, 24.

The hydraulic slave cylinder 45, the direction of action of which is opposed to the spring force, is connected by means of the hydraulic line 43 running in the bar 12 to the master cylinder 41, on which the user can act at the other end of the bar 12 by means of the release lever 18.

When the user actuates the release lever 18, liquid is displaced in the master cylinder and conveyed to the slave cylinder. The latter works against the disc spring assemblies 42 and relieves the gripper clamp. The gripper clamp 26 opens, and movement about the two axes of rotation A1, A2 becomes possible. If the operator releases the release lever 18, the spring assemblies 42 push the slave cylinder back and act with their force on the gripper clamp 26 again, so that the system is locked.

The embodiment thus provides a rotary mechanism about two mutually perpendicular axes A1, A2 that are clamped simultaneously by a clamping mechanism 28, and a locking principle in which the closing force of spring assemblies is applied and the operator only has to apply a force in order to release. When the operator releases the release lever 18, the pivot joint 16 automatically falls back into the secure locked position. It is thus possible to prevent an extension bar from falling down with a patient's leg in an uncontrolled manner when the operator unintentionally lets go of the extension bar.

In the embodiment shown here, two guide bodies are used for the pivot joint that rest on the horizontal flat surfaces 38 of the guide ring 36 and can be swiveled about a vertical axis. The outer surfaces of the two guide bodies form a common cylinder lateral surface whose axis A2 is aligned horizontally and, in the home position, perpendicular to the longitudinal axis of the patient. This common cylinder lateral surface is covered by a gripper clamp 26 that is connected to the bar 12 and, when in the untensioned state, allows the bar to move rotationally around the cylinder lateral surface. If this gripper clamp 26 is now closed, then not only is the normal force between the cylindrical outer surface 22a, 24a of the guide bodies 22, 24 and gripper clamp 26 increased, but also the normal force between the flat surfaces between the guide bodies 22, 24 and the guide ring 36. In this way, both movements can be locked and released with one operation.

It is also conceivable, however, for differently shaped articulation elements to be used instead of the guide bodies, provided that a joint can be realized that can be rotated about at least two axes of rotation, and provided that a clamping mechanism can be realized by means of which the movement of the joint on both axes can be locked simultaneously.

The medical support arm according to the disclosure has the advantage that safe operation can be ensured, because if a user accidentally drops the support arm with or without a patient leg attached thereto, the pivot joint that allows the support arm to move relative to an operating table is automatically locked.

The support arm therefore cannot fall to the ground in an uncontrolled manner. The release lever 18 and hand grip 40 mounted at the foot end of the patient enable the user to guide and support the support arm with both hands during adjustment, so that a safe and ergonomic adjustment of the position of the support arm 10 is possible.

The described clamping mechanism 28, in conjunction with the selected configuration of the pivot joint 16 as well as the holding end 13 of the support arm 10, allows the pivot joint 16 to be locked reliably in spite of the strong forces and torques acting on the pivot joint due to the long length of the support arm 10. With the locking mechanism that is known from WO 2007/080454 A2, in which a simple handle 118 and a ball joint is used, the high torques that occur due to the fact that the long support arm 10 described here is connected to the operating table 10 beyond the patient's hip, cannot be reliably absorbed. In the inventive solution described here, the required strong clamping forces are made possible particularly by the hydraulic system and the large transmission ratio (e.g., 1:10) of the eccentric lever 46. By virtue of the large lever arm of the release lever 18, the user is able to overcome the strong clamping forces with little effort.

This disclosure includes pivot joints and clamping mechanisms per se, medical support arms and extension bars, tables including medical support arms and clamping bars, and methods of using all devices and elements disclosed herein.

The exemplary embodiments described herein are illustrative and not limiting. The various features herein can be used in any reasonable combination.

The invention claimed is:

1. A medical support arm, comprising:
   a holding end for gripping and operating the support arm;
   a coupling end for connecting the support arm to a patient support;
   a coupling-end pivot joint for swiveling the support arm about a pivot axis (A1) and tilting the support arm about a tilt axis (A2) that intersects with the pivot axis;

a clamping mechanism with which the pivot joint can be selectably:
  a) locked so that a rotation of the support arm both about the pivot axis and the tilt axis is prevented; and
  b) released so that the support arm can rotate freely about both axes (A1, A2);
a release lever located at the holding end configured for releasing the clamping mechanism;
a support bar for supporting a medical device that extends between the holding end and the coupling end; and
a force transmission device that is arranged in and/or on the support bar for transmitting a releasing force from the release lever to the clamping mechanism,
wherein the pivot joint:
  a) allows the support arm to rotate exclusively about the tilt axis (A2) and the pivot axis (A1);
  b) comprises a tilting device for tilting the support arm about the tilt axis (A2), the tilting device comprising a tilting element and a cylindrical sliding surface of a central body, and the tilting element is mounted on the central body so that the cylindrical sliding surface of the central body and the tilting element can rotate relative to one another about the tilt axis (A2);
  c) a pivot mechanism configured for swiveling the support arm about the pivot axis (A1), the pivot mechanism having a guide ring and a pair of ring guide surfaces receiving the guide ring, so that the guide ring and the pair of ring guide surfaces can rotate relative to one another about the pivot axis (A1); and
  d) comprises the central body that is located in the center of the pivot joint and on which the cylindrical sliding surface and the pair of ring guide surfaces are formed;
wherein the tilting element, as part of the clamping mechanism, also acts as a gripper clamp in such a way that it secures both the tilting device and the pivot mechanism against rotation when tightened around the central body,
wherein the central body comprises two mutually mirror-inverted guide bodies each comprising one of the pair of ring guide surfaces defining a cavity therebetween and the guide ring comprises a top flat surface resting against the ring guide surface of one of the guide bodies and a bottom flat surface resting against the ring guide surface of the other guide body.

2. The medical support arm according to claim 1, wherein the cylindrical sliding surface extends once completely around the tilt axis (A2).

3. The medical support arm according to claim 1:
wherein a portion of the cylindrical sliding surface is formed on the outside of each guide body, so that the two parts together form the entire cylindrical sliding surface.

4. The medical support arm according to claim 1, further comprising a connecting piece at the holding end, wherein the connecting piece supports the guide ring and has a coupling for connecting to the patient support.

5. The medical support arm according to claim 4, wherein the guide ring is received between prongs of a forked end of the connecting piece.

6. The medical support arm according to claim 1, wherein the clamping mechanism comprises a spring assembly that biases the clamp into the locked position.

7. The medical support arm according to claim 6, wherein the clamp mechanism further comprises an eccentric assembly via which the spring assembly acts on the gripper clamp.

8. The medical support arm according to claim 7, wherein the spring assembly comprises at least one disc spring, and wherein the eccentric assembly comprises at least one eccentric lever.

9. The medical support arm according to claim 8, wherein each eccentric lever has an eccentric end in the form of an eccentric disc and an operating end, wherein the operating end is connected to a disc spring, and wherein the eccentric end is connected to an extremity of the gripper clamp through which the axis of rotation (Y-Y) of the eccentric lever passes.

10. The medical support arm according to claim 1, wherein the force transmission device comprises:
  a master cylinder that is arranged at the holding end;
  a slave cylinder that is arranged at the coupling end; and
  a hydraulic line that extends through the interior of the support bar and connects the master cylinder to the slave cylinder.

11. The medical support arm according to claim 10, wherein the slave cylinder hydraulically releases the bias of the spring assembly upon actuation of the release lever.

12. The medical support arm according to claim 1, wherein the pivot axis (A1) and the tilt axis (A2) are each aligned perpendicular to a longitudinal axis (X-X) of the medical support arm and perpendicular to each other.

13. The medical support arm according to claim 1, wherein the medical support arm is an extension bar.

14. The medical support arm according to claim 1, further comprising a hand grip located at the holding end adjacent to the release lever, so that when the clamp mechanism is released, the medical support arm can be held by a single person with a first hand on the release lever and a second hand on the hand grip.

15. An operating table comprising:
a patient support surface, and
a support arm according to claim 1;
wherein said patient support comprises at least part of the operating table.

16. The medical support arm according to claim 1:
wherein the medical support arm is an extension bar;
wherein the extension bar has a carriage thereon, the carriage being slideable axially along the extension bar;
wherein the carriage carries a device shaped for holding the foot of a patient which is movable with the carriage.

17. A medical support arm, comprising:
a holding end for gripping and operating the support arm;
a coupling end for connecting the support arm to a patient support;
a support bar for supporting a medical device that extends between the holding end and the coupling end; and
a pivot joint provided at the coupling end, the pivot joint comprising:
  a central body comprising two mutually mirror-inverted guide bodies that each comprise a ring guide surface defining a cavity therebetween;
  a connecting piece having a first end with a coupling for connecting the support arm to the patient support and a second end comprising a guide ring configured to be received in the cavity between the guide bodies so as to be rotatable about a pivot axis, the guide ring comprising a top flat surface resting against the ring guide surface of one of the guide bodies and a bottom flat surface resting against the ring guide surface of the other guide body; and
  a gripper clamp securely connected to the support bar and mounted on a cylindrical sliding surface provided on an exterior of the guide bodies of the central body so as to be rotatable about a tilt axis that intersects with the pivot axis, wherein the gripper clamp is configured to be to be tightened around the central body so that a rotation of the support arm both about the pivot axis and the tilt axis is prevented, and released from around the central body so that the support arm can rotate freely about the pivot axis and the tilt axis.

18. The medical support arm according to claim 17, further comprising a release lever located at the holding end configured for releasing the gripper clamp.

19. The medical support arm according to claim 18, further comprising a force transmission device that is arranged in and/or on the support bar for transmitting a releasing force from the release lever to the gripper clamp.

* * * * *